A United States Patent [19]

Parry et al.

US005137626A

[11] Patent Number: 5,137,626
[45] Date of Patent: Aug. 11, 1992

[54] SOLID-PHASE EXTRACTION TUBES CONTAINING SULFONAZIDE BONDED-PHASE EXTRACTANTS

[75] Inventors: Ritchard C. Parry, Port Matilda; Daryl J. Gisch, Boalsburg, both of Pa.

[73] Assignee: Rohm and Haas Company, Philadelphia, Pa.

[21] Appl. No.: 313,641

[22] Filed: Feb. 21, 1989

[51] Int. Cl.⁵ ............................................. B01D 15/08
[52] U.S. Cl. ............................ 210/198.2; 210/502.1; 210/656; 436/178; 436/527; 436/816; 436/901; 502/407; 530/834; 552/4; 552/5; 556/427
[58] Field of Search ................... 210/198.2, 502.1, 635; 502/401, 402, 407; 436/816, 161, 178, 527, 901; 552/4, 5; 526/279; 556/427; 530/834

[56] References Cited

U.S. PATENT DOCUMENTS

| | | | |
|---|---|---|---|
| 3,697,551 | 10/1972 | Thomson | 552/4 |
| 4,401,598 | 8/1983 | Karl et al. | 552/4 |
| 4,640,909 | 2/1987 | Ramsden et al. | 502/407 |
| 4,650,784 | 3/1987 | Ramsden et al. | 210/198.2 |
| 4,680,120 | 7/1987 | Ramsden et al. | 210/656 |
| 4,680,121 | 7/1987 | Ramsden et al. | 210/656 |

OTHER PUBLICATIONS

J. A. Vinson and D. J. Lopatofsky, "Journal of Analytical Toxicology", vol. 9, Jan./Feb. 1985, pp. 6-9.
M. A. Elsohly, H. N. Elsohly, A. B. Jones, P. A. Dimson, and K. E. Wells, "Journal of Analytical Toxicology", vol. 7, Nov./Dec. 1983, pp. 262-264.
H. H. McCurdy, L. J. Lewellen, L. S. Callahan, and P. S. Childs, "Journal of Analytical Toxicology", vol. 10, Sep./Oct. 1986, pp. 175-177.

*Primary Examiner*—Robert A. Dawson
*Assistant Examiner*—Sun Uk Kim
*Attorney, Agent, or Firm*—John E. Taylor, III

[57] ABSTRACT

The bonded phases generated from the reaction of aliphatic and aromatic azidosilanes with silica gel are suitable for use as packings in solid phase extraction columns for cleanup of urine samples for analysis of acid metabolites of cannabinoids. Such bonded phases are unique in their ability to selectively retain the acid metabolites of cannabinoids from a urine sample matrix.

8 Claims, 5 Drawing Sheets

SOLID-PHASE EXTRACTION TUBES CONTAINING SULFONAZIDE BONDED-PHASE EXTRACTANTS

FIELD OF THE INVENTION

This invention relates to solid phase extraction packing materials and an extraction procedure useful for the cleanup of urine samples for the analysis of acidic metabolites of cannabinoids in urine.

BACKGROUND OF THE INVENTION

The continued increase in marijuana abuse has created an even greater demand for sensitive, rapid and reliable methods for confirming the presence of this drug in biological samples. Confirmation of the presence of the drug is important in initially detecting marijuana users as well as assisting drug counseling programs in monitoring compliance with rehabilitation programs.

Marijuana abuse is detected by identifying the presence of metabolites of the major psychoactive constituent of marijuana, delta-9-tetrahydrocannabinol, in biological fluids. Urine, because of its less invasive and more convenient sampling process, is the biological fluid most often analyzed for marijuana abuse. The major metabolite of delta-9-tetrahydrocannabinol found in urine is 11-nor-delta-9-tetrahydrocannabinol-9-carboxylic acid (THC-COOH) existing in both a free acid and a conjugated (glucuronide) form. Many analytical procedures using gas chromatography, high performance liquid chromatography, thin layer chromatography, gas chromatography-mass spectrometry, radioimmunoassay and enzyme multiplied immunoassay have been developed for determining the presence of THC-COOH in urine. However, the sensitivity and, more importantly, the reliability of these methods are hindered by inadequacies of the techniques used in preparing urine samples for analysis. Current methods of sample preparation, using techniques such as thin layer chromatography, liquid-liquid extraction and other solid phase extraction techniques commonly suffer from low drug recovery, incomplete removal of interfering urine components, and/or long preparation times.

Measurement of THC-COOH in urine is considerably complicated by the complexity of the urine matrix. The large number of organic acids present in urine make extraction of THC-COOH quite difficult. Many of these organic acids exhibit chromatographic properties similar to THC-COOH and therefore may interfere with the measurement of the drug metabolite. Therefore, selective extraction of THC-COOH from the urine sample matrix is essential to providing the sensitivity and reliability required for confident drug monitoring.

Typical urine screens for THC-COOH and many other abused-drugs are performed using thin layer chromatography or the Enzyme Multiplied Immunoassay Technique (EMIT) of Syva Company. Positive results are then confirmed using a second more specific test. Confirmation is usually obtained using gas chromatography-mass spectrometry techniques, however other chromatographic techniques may be employed. The use of these techniques has created a need for a more efficient sample cleanup technique. A bonded phase chromatographic packing that allows selective washing of impurities without removing the THC-COOH and/or permits selective elution of the THC-COOH without removing impurities would be highly desirable. A clean, concentrated extract with good metabolite recovery will allow for much more sensitive confirmation analyses. A clean extract will also aide in maintaining the integrity of the instrumentation used in confirmation.

Several existing patents, such as U.S. Pat. Nos. 4,640,909; 4,650,784; 4,680,120 and 4,680,121, and journal publications, such as M. ElSohly et al, Analysis of the Major Metabolite of delta-9-tetrahydrocannabinol in Urine, Journal of Analytical Toxicology, vol. 7, November/December 1983, pp. 262-264; J. Vinson et al, A Semi-Automated Extraction and Spotting System for Drug Analysis by TLC, Journal of Analytical Toxicology, vol. 9, January/Febuary 1985, pp. 6-7 H. McCurdy et al, Evaluation of the Ion Trap Detector for the Detection of 11-nor-delta-9-tetrahydrocannabinol-9-carboxylic acid in Urine After Extraction by Bonded-Phase Adsorption, Journal of Analytical Toxicology, vol. 10, September/October 1986, pp. 175-177, report the use of solid phase extraction in the analysis of THC-COOH in urine. All of this prior art uses bonded phases and extraction procedures significantly different from those represented in this invention.

The four United States patents, held by J. T. Baker, disclose the use of silica based bonded phases with ether, ester, thiol ether and alkyl function groups for extracting THC-COOH from urine using a reverse phase or hydrogen bonding mechanism. The processes for the extraction of the drug metabolite also use different solutions and solvents for conditioning and washing the bonded phase as well as eluting the drug metabolite from the bonded phase than those disclosed in this invention.

The work of ElSohly et al and McCurdy et al discuss the use a bonded phase, produced by Analytichem International, for the extraction of THC-COOH from urine. The chemistry of the bonded phase is not disclosed in this work but once again different solutions and solvents are used in the conditioning, washing and elution of the bonded phase than those used in this invention. The work of Vinson et al discusses the use of an ion exchange resin in the extraction of THC-COOH. Once again the extraction process differs significantly from the process disclosed in this invention.

The invention of this document uses a unique bonded phase which contains a sulfonylazide grafted to silica through a reversed phase side chain which isolates THC-COOH from urine. Absolute recovery of the THC-COOH is also significantly improved when using the invention as compared to the recoveries obtained from the previously published methods.

OBJECTS OF INVENTION

An object of the invention is the development of a sample pretreatment that allows for improved and more reproducible analysis of THC-COOH in urine.

Another object of the invention is the development of a bonded phase, consisting of a support and a sulfonylazide functional group linked to the support through a spacer of 2 to 10 carbon units in length, for the solid phase extraction of 11-nor-delta-9-tetrahydrocannabinol-9-carboxylic acid from urine.

Yet another object of the invention is the development of a bonded phase for the solid phase extraction of THC-COOH that allows impurities from a urine sample matrix to be selectively washed from the phase providing isolation of the THC-COOH in a relatively pure extract.

Still another object of the invention is the development of a bonded phase for the pretreatment of urine samples containing THC-COOH resulting a concentration of the THC-COOH sample on the bonded phase.

A further object of the invention is the development of an extraction procedure for the selective washing of the impurities from the urine sample matrix from the bonded phase.

Another object of the invention is the development of an extraction procedure for the isolation of THC-COOH in a relatively pure extract.

A further object of the invention is the development of an extraction procedure for the concentration of a urine sample containing THC-COOH on the bonded phase.

A still further object of the invention is the development of a chemically specific extraction procedure that concentrates and isolates THC-COOH to an analyte that may be conveniently analyzed by numerous conventional analytical techniques.

Another object of the invention is the development of an extraction method to provide improved and more reproducible analysis of THC-COOH in urine.

Other objects of the invention will be apparent from the following specification.

BRIEF DESCRIPTION OF THE INVENTION

A bonded phase and solid phase extraction procedure for the extraction of a more highly purified and concentrated form of THC-COOH at a higher level of recovery from urine is provided by the reaction product obtained from the reaction of silica with alkoxysilanes of the formulas:

in which R is an aliphatic chain from 2 to 10 carbon units in length and where aliphatic can be defined as a straight, branched or cyclic carbon chain. $R_1$, $R_2$ and $R_3$ are reactive silanes. These reactive silanes can be the same or different and are selected from halogens, hydroxyl groups or alkoxy groups with aliphatic carbon chains from one to four carbon units long. $R_4$ is an aliphatic chain from 0 to 4 carbon units in length.

The extraction procedure, consisting of a mild acid conditioning of the bonded phase followed by sample addition and packing washes with polar and ionic solutions to remove urine impurities and sample elution with an organic solvent, provides a purer extract and significantly greater recovery of the THC-COOH from urine than previously used or available bonded phases. The pure extract and increased recovery allow quantitation of the THC-COOH at much lower levels providing a more sensitive and more accurate analysis.

BRIEF DESCRIPTION OF DRAWINGS

A brief description of the figures follows.

FIGS. 1-3 depict the analysis of THC-COOH by gas chromatography with flame ionization detection using a 30 m×0.25 mm I.D. (0.25 micrometer df) SPB-35 capillary gas chromatography column. The analytical conditions for this column were a helium carrier gas at a flow rate of 32.7 cm/sec, 1 μl injection volume, splitless injection with a 30 second delay and 50:1 split ratio, an injectector temperature of 260° C., a detector temperature of 290° C., and a detector sensitivity of $2 \times 10^{-11}$ AFS. The temperature program used with the column started with a 2 minute hold at 220° C. followed by a linear temperature ramp to 290° C. at a rate of 10° C. per minute. The final temperature was held for 12 minutes.

FIG. 4-6 depict the analysis of THC-COOH by gas chromatography-mass spectrometry using a 15 m×0.25 mm I.D. (0.25 micrometer df) SPB-5 capillary gas chromatography column. The analytical conditions for this column were a helium carrier gas at a flow rate of 29.8 cm/sec, 1 μl injection volume, splitless injection with a 30 second delay and a 50:1 split ratio and an injector temperature of 260° C. The temperature program used with the column started with a 2 minute hold at 220° C. followed by a linear temperature ramp to 290° C. at a rate of 10° C. per minute. The final temperature was held for 10 minutes. The mass spectrometer was programmed for selected ion monitoring over the ranges of m/z 364.610 to m/z 376.613 and m/z 471.642 to m/z 492.648. The scan rate over the two ranges was 0.518 scans per second.

FIGS. 7-9 depicts the analysis of THC-COOH by high performance liquid chromatography using ultraviolet detection. The analytical column used was a 25 cm×4.6 mm I.D. (5 micrometer) octyldecylsilane column with a 2 cm×4.6 mm I.D. (5 micrometer) octyldecylsilane guard column. The mobile phase consisted of a 55:45 mixture of acetonitrile and 2% (v/v) acetic acid in deionized water. A flow rate of 2.5 ml/min was maintained and the column operated at a temperature of 30° C. The injection volume was 100 μl. The detector was operated at a wavelength of 280 nm and a sensitivity of 0.004 AUFS.

FIGS. 10-12 depicts a comparison of extraction methods analyzed by gas chromatography with flame ionization detection. The analytical column used in this work was a 30 m×0.25 mm I.D. (0.25 micrometer df) SPB-35 capillary gas chromatography column. The analytical conditions for this column were a helium carrier gas at a flow rate of 32.7 cm/sec, 1 μl injection volume, splitless injection with a 30 second delay and a 50:1 split ratio, an injector temperature of 260° C., a detector temperature of 290° C. and a detector sensitivity of $2 \times 10^{-11}$ AFS. The temperature program used with the column started with a 2 minute hold at 220° C. followed by a linear temperature ramp to 290° C. at a rate of 10° C. per minute. The final temperature was held for 12 minutes.

DETAILED DESCRIPTION OF THE INVENTION

The alkoxysilanes reacted with the silica gel can be any silane conforming to the previously described formulas. In these formulas the spacer chain in the R group is preferably a straight chain with a length of seven carbons or the R group is a straight chain with a length of two carbon units.

The reaction product is useful as a packing in solid phase extraction for the purification of THC-COOH in human urine. Such bonded phase silica products are obtained by reaction of previously described alkoxysilanes with silica gel having an average particle diameter from 3 to 177 micrometers and an average pore size from 60 to 300 angstrom units.

The silica based bonded phase products of this invention can be prepared in accordance with the following steps:

A. reacting either particulate silica gel having an average particle diameter from 3 to 177 micrometers and an average pore size from 40 to 300 angstrom units in an aprotic organic solvent slurry with an alkoxysilane of the previously defined formulas, said reaction being conducted at ambient to refluxing temperatures for about 4 to approximately 24 hours;

B. recovering the resultant solid fraction from the mixture; and

C. the solid fraction washed with aprotic and protic organic solvents to remove unbound reaction products and dried at a temperature not exceeding 70° C.

The reaction takes place in one step as shown. An alkoxysilane with an aliphatic seven carbon length spacer chain and an alkoxysilane with an aromatic ring and aliphatic two carbon length spacer chain are used as an exemplary silane reagents.

Step 1: Silica hydroxyls and the ethoxy groups on the silane react to form Si-O-Si bonds and free ethanol, with some residual ethoxy groups remaining unreacted:

-continued or:

Among the aprotic organic solvents suitable for preparing the silica gel slurry or washing the reaction product are aliphatic hydrocarbons such as, for example, hexane, heptane, cyclohexane and the like; aromatic hydrocarbons such as, for example, benzene, toluene, xylene and the like; chlorinated methanes such as, for example, methylene chloride, chloroform, carbon tetrachloride and the like. Among the protic solvents suitable for washing the reaction product are methanol, acetonitrile, acetone, ethanol, isopropyl alcohol, tetrahydrofuran, ethyl acetate and the like.

In general, about 30 to 75 grams of the silane is used to react with each 100 grams of silica. The reaction may be conducted at ambient temperature although elevated temperatures up to the refluxing temperature of the reaction solvent system may be utilized to enhance the rate of the reaction. The reaction proceeds readily to completion within 4 to 24 hours.

The resultant solid fraction is recovered from the reaction mixture by conventional physical means, for example, filtration, centrifugation and the like. Filtration is typically suitable for particle sizes of 5 micrometers or larger. Centrifugation is typically suitable for particles smaller than 5 micrometers.

The subsequent reaction products constitute a new and useful bonded phase for the purification and concentration of THC-COOH in urine samples. An example of the methodology suitable for purification and concentration of THC-COOH is similar to that reported in the literature using other but much less effective and efficient bonded phases and methods, for example, the methodology disclosed by M. ElSohly, *J. Analytical Toxicology*, Vol. 7, pp. 262-264, 1983 H. E. Ramsden et al. U.S. Pat. No. 4,640,909 issued Feb. 3, 1987.

The following is only one possible embodiment of the procedure for using the bonded phase extractant of the present invention. For example, the bonded phases of this invention are packed in solid phase extraction tubes. A solid phase extraction tube is described as a vessel manufactured from an appropriate material including but not limited to glass, stainless steel, aluminum, titanium or moldable plastic, for example polyethylene, polypropylene, delrin or other such plastic. Packing is held in place in the solid phase extraction tube using an appropriate porous material manufactured from material including but not limited to glass stainless steel, glass wool or plastic, for example polyethylene, polypropylene, delrin or other such plastic. Such a solid phase extraction tube is packed with an appropriate quantity of the bonded phases of the present invention, as for example, 100 mg when the dimensions of the tube are a cylinder of length 6.5 cm, an inner diameter of 1 cm with a male Leurlok ® fitting molded to one end of the cylinder. For such a tube and quantity of bonded phase extractant, the tube is then conditioned with 2 ml of methanol or other organic solvent such as aprotic solvents or protic solvents, for example, acetonitrile, acetone, ethanol, isopropyl alcohol, tetrahydrofuran and the like. The packing is then conditioned with 1 ml of an aqueous 1% acetic acid solution to adjust the pH of the packing for complete retention of the metabolite (care must be taken not to let the column dry out prior to sample addition). Other acids can be used in place of the acetic acid such as phosphoric acid, hydrochloric acid, sulfuric acid, perchloric acid, nitric acid, hydrobromic acid, hydriodic acid and the like. Two milliliters of the hydrolyzed sample is then added to the tube. The rest of the hydrolyzed sample is added to a reservoir attached to the tube using an adaptor. The sample is then passed through the tube at a slow, dropwise flow rate (approximately 500 l/min.). The reservoir and adaptor are then removed and the tube washed with two 1 ml aliquots of an aqueous 20% acetone solution to remove polar impurities from the packing. Other water miscible organic solvents can be used in place of acetone such as methanol, acetonitrile, tetrahydrofuran, ethanol, isopropyl alcohol, ethyl acetate and the like. The tube is then washed with 1.5 ml of an aqueous 0.01M KH PO solution. Other ionic strength modifiers can be used in place of KH PO such as potassium phosphate (dibasic), sodium phosphate (monobasic), sodium phosphate (dibasic), sodium acetate, sodium chloride, ammonium 30 acetate, sodium sulfate and the like. The bonded phase is then washed with 500 l of an aqueous 0.01M Na HPO solution to remove ionic impurities from the packing. Other ionic strength modifiers can be used in place of Na HPO such as sodium phosphate (monobasic), potassium phosphate (monobasic), potassium phosphate (dibasic), sodium acetate, sodium sulfate, sodium chloride, ammonium acetate and the like. The final wash is 500 l of an aqueous 1% acetic acid solution used to orient the pH of the packing in the proper range for complete removal of the metabolite. Once again other acids can be used in place of acetic acid. The metabolite is eluted from the tube using 1 ml of methanol and collected in a silanized glass vial. Once again, other aprotic or protic solvents could be used in place of the methanol. The methanol is then evaporated under nitrogen. The sample is then reconstituted in a suitable solvent or derivatized. Non-derivatized samples may be analyzed by high performance liquid chromatography, thin layer chromatography, UV-visible spectroscopy, mass spectrometry, mass spectrometry-mass spectrometry, liquid chromatography-mass spectrometry, radioimmunoassay (RIA), Enzyme-Multiplied Immunoassay Technique (EMIT), Enzyme-Linked Immunosorbent Assay (ELISA) or other such analytical techniques. Derivatized samples may be analyzed by gas chromatography, high performance liquid chromatography, UV-visible spectroscopy, thin layer chromatography, mass spectrometry, gas chromatography-mass spectrometry, liquid chromatography-mass spectrometry, mass spectrometry-mass spectrometry, RIA, EMIT, ELISA or other such analytical technique.

Exemplary of the preparation of the new sulfonylazide bonded phases according to the invention are the following representative examples.

EXAMPLE 1

To 100 grams of 40 micrometer silica was added 5700 ml of toluene and 1000 ml of 50% 2-(triethoxysilyl)-hexylsulfonylazide in methylene chloride. The mixture is gently heated until the silane and solvents are completely dispersed (approximately 10 minutes). Add 900 g of 40 micrometer silica gel to the mixture, gently swirling until a homogeneous mixture is obtained. The mixture is then brought to a gentle reflux for six hours. The mixture is cooled and washed three times with 2 liters of toluene. The bonded phase is then decanted onto a sintered glass funnel and washed with 2 liters of methanol. The phase is then dried under reduced pressure at approximately 70° C.

The bonding process can be summarized as follows:
a. Mix toluene, a 50% solution of 2-(triethoxysilyl)-hexylsulfonylazide in methylene chloride and silica gel.
b. Gently reflux the mixture for 4 to 24 hours.
c. Cool the reaction product to room temperature.
d. Wash the reaction product with toluene.
e. Wash the reaction product with methanol.
f. Dry the reaction product under reduced pressure at a temperature not exceeding 70° C. The dried bonded phase product is now ready to be packed in a solid phase extraction tube and used for the extraction of THC-COOH from urine.

EXAMPLE 2

To 100 g of 40 micrometer silica gel was added 600 ml of toluene and 70 ml of 50% 2-(trimethoxysilyl)ethylphenyl sulfonylazide in methylene chloride. The mixture was suspended by shaking and refluxed for 7 hours. The mixture was cooled, filtered and washed three times with 200 ml of toluene followed by three 500 ml washes with methanol. The resulting bonded phase was oven dried at a temperature no greater than 70° C.

The bonding process can be summarized as follows:
a. Mix silica gel, toluene and a 50% mixture of 2-(trimethoxysilyl)ethylphenylsulfonylazide.
b. Gently reflux the mixture for 4 to 24 hours.
c. Cool the reaction product to room temperature.
d. Wash the reaction product with toluene.
e. Wash the reaction product with methanol.
f. Dry the reaction product at reduced pressure at a temperature not exceeding 70° C. The dried bonded phase product is now ready to be packed in a solid phase extraction tube and used for the extraction of THC-COOH from urine.

As exemplary of the use of the bonded phase products of this invention in the cleanup of urine samples for analysis of cannabinoids, reference may be made to the following Example. In the following Example the urine sample is first hydrolyzed to convert all of the conjugated metabolite to the free acid form for chromatographic processing according to this invention. Typically such hydrolysis of a urine sample is conducted in the following manner. Five milliliters of urine, 5 ml of deionized water and 500 µl of 10 M KOH are placed in a silanized glass container. The sealed container is then heated for 15 minutes at 60° C. in a hot water bath. The solution is then cooled and the pH of the solution adjusted between 4 and 5 with glacial acetic acid. Urine samples treated in this manner will henceforth be referred to as hydrolyzed samples.

EXAMPLE 3

A standard 3 ml size polypropylene (serological grade) solid phase extraction tube with polyethylene frits (20 micrometer pores) is packed with 100 mg of either the bonded phase described in Example 1 or 100 mg of the bonded phase described in Example 2. The tube is then conditioned with 2 ml of methanol followed by 1 ml of an aqueous 1% acetic acid solution to adjust the pH of the packing for complete retention of the metabolite (care must be taken not to let the column dry out prior to sample addition). Two ml of the hydrolyzed sample is then added to the tube. The rest of the hydrolyzed sample is added to a reservoir attached to the tube using an adaptor. The sample is then passed through the tube at a slow, dropwise flow rate (approximately 500 $\mu$l/min.). The reservoir and adaptor are then removed and the tube washed with two 1 ml aliquots of an aqueous 20% acetone solution to remove polar impurities from the packing. The tube is then washed with 1.5 ml of an aqueous 0.01 M $KH_2PO_4$ solution. The bonded phase is then washed with 500 $\mu$l of an aqueous 0.01 M $Na_2HPO_4$ solution to remove ionic impurities from the packing. The final wash is 500 $\mu$l of an aqueous 1% acetic acid solution used to orient the pH of the packing in the proper range for complete removal of the metabolite. The metabolite is eluted from the tube using 1 ml of methanol and collected in a silanized glass vial.

The extraction process can be summarized as follows:
a. Condition the bonded phase with methanol.
b. Condition the bonded phase with an aqueous solution of acetic acid.
c. Pass the hydrolyzed sample through the bonded phase at a slow dropwise rate.
d. Wash the bonded phase with an aqueous solution containing acetone.
e. Wash the bonded phase with an aqueous solution of potassium phosphate (monobasic).
f. Wash the bonded phase with an aqueous solution of sodium phosphate (dibasic).
g. Wash the bonded phase with an aqueous solution of acetic acid.
h. Thoroughly dry the bonded phase.
i. Elute the THC-COOH from the bonded phase with methanol.

The methanol is then evaporated under nitrogen. The sample is then reconstituted in mobile phase for HPLC or TLC analysis or derivatized for GC analysis. Several different derivatives can be prepared for GC analysis. Pentafluoro derivatives are typically used for GC analysis with electron capture detection. Methylated or trimethylsilyl derivatives of the drug metabolite are typically formed for GC analysis where flame ionization or mass selective detection are used. A trimethylsilyl derivative of the acid metabolite is easily formed by reconstituting the evaporated sample extract in 25 $\mu$l of bis(trimethylsilyl)-trifluoroacetamide (BSTFA) and heating the solution for 10 minutes at 70° C.

Figure 1:
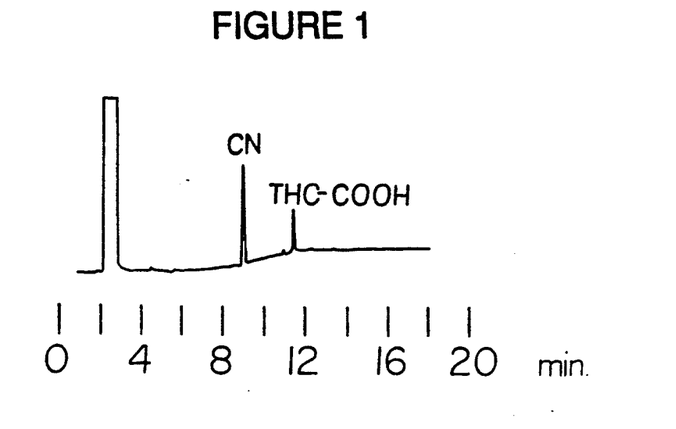
FIG. 1 depicts a typical FID chromatogram obtained from a THC-COOH standard containing the internal standard cannabinol (CN).
Figure 2:
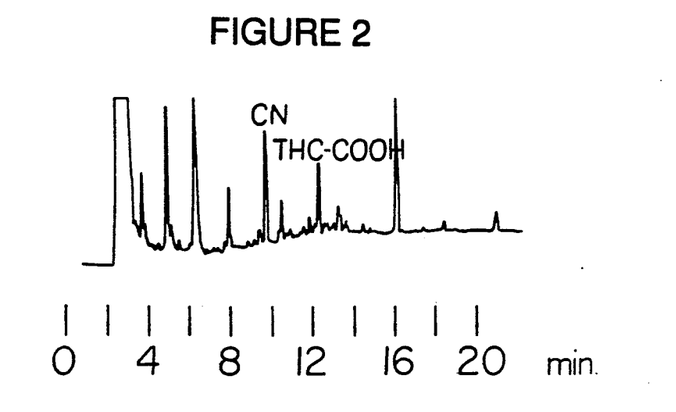
FIG. 2 depicts a typical FID chromatogram of an extracted urine sample. The initial urine concentration of THC-COOH was 50 ng/ml.
Figure 3:
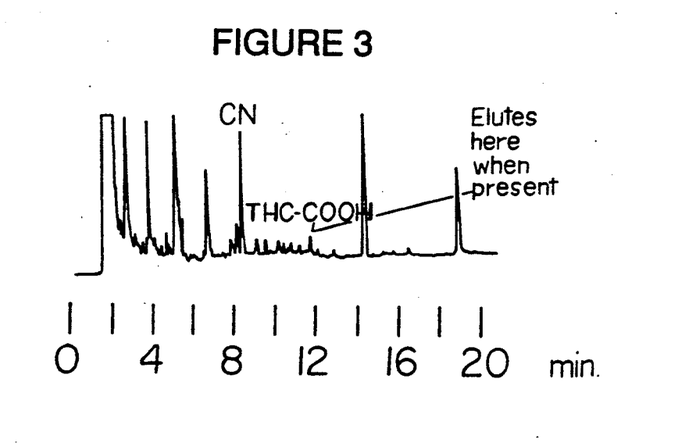
FIG. 3 depicts a typical FID chromatogram of an extracted urine blank.

There are numerous chromatographic supports and analytical conditions sited in the technical literature for the analysis of THC-COOH. However, NIDA and other government agencies require that GC-MS be used for the confirmation of the presence of THC-COOH in urine. Examples of three analytical techniques are shown in FIGS. 1 through 9. FIGS. 1 through 3 show detection of THC-COOH in its trimethylsilyl derivatized form using a 30 m×0.25 mm I.D. (0.25 micrometer df) SPB-35 capillary gas chromatography column with flame ionization detection. The analytical conditions for this column were a helium carrier gas at a flow rate of 32.7 cm/sec, 1 $\mu$l injection volume, splitless injection with a 30 second hold, an injector temperature of 260° C., a detector temperature of 290° C. and a detector sensitivity of $2 \times 10^{-11}$ AFS. The temperature program used with the column started with a 2 minute hold at 220° C. followed by a linear temperature ramp to 290° C. at 10° C./min with a hold at 290° C. for 12 minutes. FIGS. 1 through 3 represent typical chromatograms obtained from a THC-COOH standard, an extracted urine sample originally containing 50 ng/ml of THC-COOH and an extracted urine blank using the described conditions. Table 1 shows typical recoveries of derivatized THC-COOH obtained from urine samples extracted using this invention as determined by GC with flame ionization detection. The bonded phase used for these extractions is described in Example 1.

TABLE 1

| Absolute recovery of THC-COOH from urine using the bonded phase of Example 1 as determined by gas chromatography with flame ionization detection. | | |
|---|---|---|
| | Absolute Recovery | |
| Trial | 50 ng/ml | 250 ng/ml |
| 1 | 83.7 | 89.0 |
| 2 | 86.9 | 92.2 |
| 3 | 85.6 | 86.4 |
| 4 | 87.2 | 88.3 |
| 5 | 84.6 | 87.7 |
| Avg ± S.D. | 85.6 ± 1.5 | 88.7 ± 2.2 |

Table 2 shows typical recoveries of derivatized THC-COOH obtained from urine samples extracted using this invention as determined by gas chromatography with flame ionization detection. The bonded phase used for these extractions is described in Example 2.

TABLE 2

| Absolute recovery of TMC-COOH from uring using the bonded phase of Example 2 as determined by gas chromatography with flame ionization detection. | |
|---|---|
| Trial | Recovery from 50 ng/ml urine sample |
| 1 | 82.3 |
| 2 | 67.4 |
| 3 | 79.2 |
| 4 | 91.0 |
| 5 | 73.4 |
| Avg. ± S.D. | 78.7 ± 8.9 |

Figure 4:
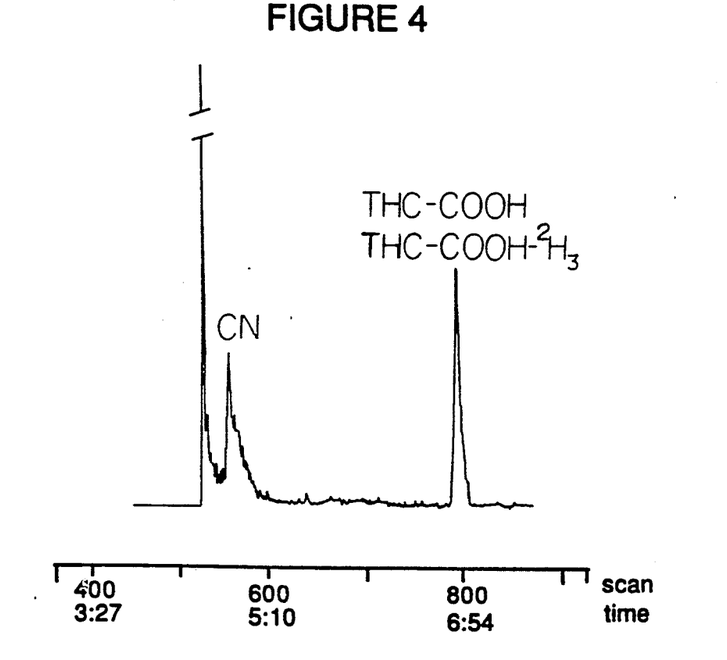
FIG. 4 depicts a typical reconstructed ion chromatogram for a THC-COOH standard containing the internal standards CN and 11-nor-delta-9-tetrahydrocannabinol-9-carboxylic acid-5'-$^2$H$_3$ (THC-COOH-H$_3$).
Figure 5:
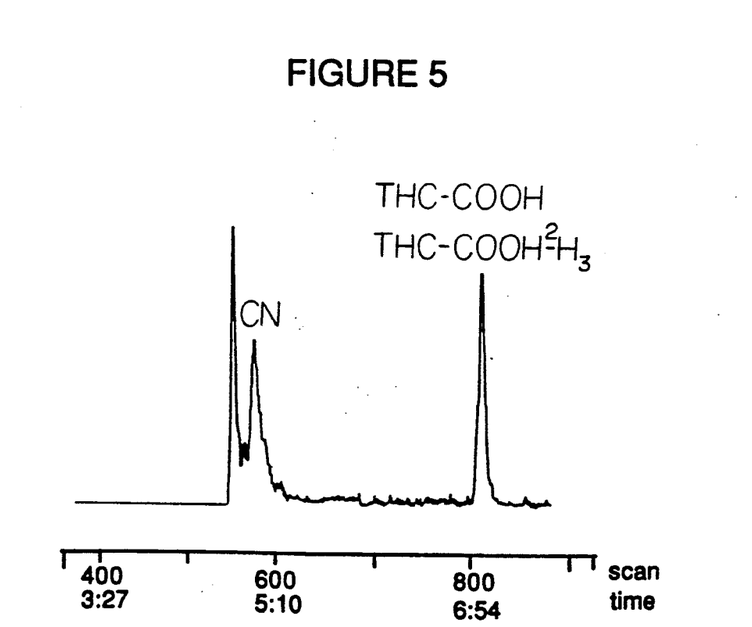
FIG. 5 depicts a typical reconstructed ion chromatogram obtained from an extracted urine sample. The initial concentration of THC-COOH in the urine sample was 50 ng/ml.
Figure 6:
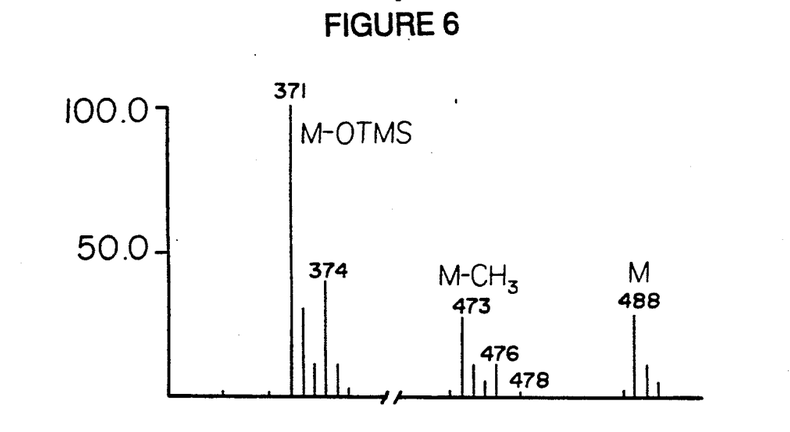
FIG. 6 depicts the mass spectrum obtained from the derivatized form of THC-COOH where M designates the parent ion, m/z 488, M-CH$_3$ designates the loss of a methyl group from the parent ion, m/z 473, and M-OTMS depicts the loss of an oxygen and trimethylsilyl group from the parent ion, m/z 371.

FIGS. 4 through 6 show the detection of THC-COOH in its trimethylsilyl derivatized form using a 15 m×0.25 mm I.D. (0.25 micrometer df) SPB-5 capillary gas chromatography column with a mass spectrometer used as the detector. The analytical conditions used with this column were a helium carrier gas at a flow rate of 29.8 cm/sec, 1 $\mu$l injection volume, splitless injection with a 30 second delay and an injector temperature of 260° C. The temperature program started with an initial 2 minute hold at 220° C. followed by a linear temperature ramp to 290° C. at a rate of 10° C./min and a hold of 10 minutes at the final temperature. The mass spectrometer was programmed for selected ion monitoring over the ranges of m/z 364.610 to m/z 376.613 and m/z 471.642 to m/z 492.648. The scan rate over the two ranges was 0.518 scans per second. FIGS. 4 and 5 represent typical chromatograms obtained from a THC-COOH standard and an extracted urine sample originally containing 50 ng/ml of THC-COOH using the described conditions. FIG. 6 shows the mass spectrum obtained from trimethylsilyl derivatized THC-COOH extracted from a urine sample originally containing 50 ng/ml of THC-COOH. The derivatized THC-COOH is identified by the m/z 488 peak representing the parent ion, m/z 473 peak representing the loss of a methyl group from the parent ion and the m/z 371 peak representing the loss of an oxygen-trimethylsilyl linkage from the parent ion. Table 3 shows typical recoveries of derivatized THC-COOH obtained from urine samples extracted using this invention as determined by GC-MS. The bonded phase used for these extractions is described in Example 1.

TABLE 3

Absolute and relative recovery of THC-COOH from urine using the bonded phase of Example 1 as deteremined by gas chromatography-mass spectrometry.

| Trial | 5 ng/ml | 50 ng/ml | 250 ng/ml |
|---|---|---|---|
| | Absolute Recovery | | |
| 1 | 108 | 96.2 | 112 |
| 2 | 87.9 | 79.2 | 110 |
| 3 | 103 | 97.0 | 113 |
| 4 | 83.1 | 115 | 97.7 |
| 5 | 89.4 | 121 | 113 |
| Avg ± S.D. | 94.3 ± 10.6 | 102 ± 16.4 | 109 ± 6.5 |
| | Relative Recovery | | |
| 1 | 86.8 | 98.8 | 92.8 |
| 2 | 109 | 84.9 | 95.5 |
| 3 | 99.8 | 85.9 | 103 |
| 4 | 89.2 | 93.8 | 91.8 |
| 5 | 102 | 97.2 | 92.6 |
| Avg ± S.D. | 97.4 ± 9.2 | 92.1 ± 6.4 | 95.1 ± 4.6 |

Table 4 shows typical recoveries of derivatized THC-COOH obtained from urine samples extracted using this invention as determined by GC-MS. The bonded phase used for these extractions is described in Example 2.

TABLE 4

Absolute and relative recovery of THC-COOH from urine using the bonded phase of Example 1 as deteremined by gas chromatography-mass spectrometry.

| Trial | Absolute Recovery | Relative Recovery |
|---|---|---|
| 1 | 78.3 | 90.1 |
| 2 | 88.9 | 95.3 |
| 3 | 82.6 | 89.3 |
| 4 | 66.5 | 92.9 |
| 5 | 77.4 | 92.2 |
| Avg. ± S.D. | 78.7 ± 8.2 | 92.0 ± 2.4 |

Figure 7:
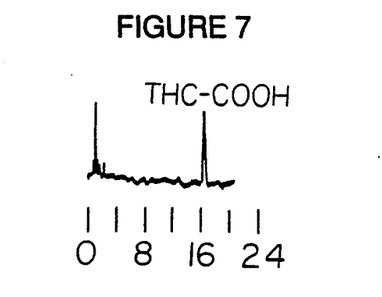
FIG. 7 depicts a typical HPLC chromatogram obtained from a THC-COOH standard.
Figure 8:
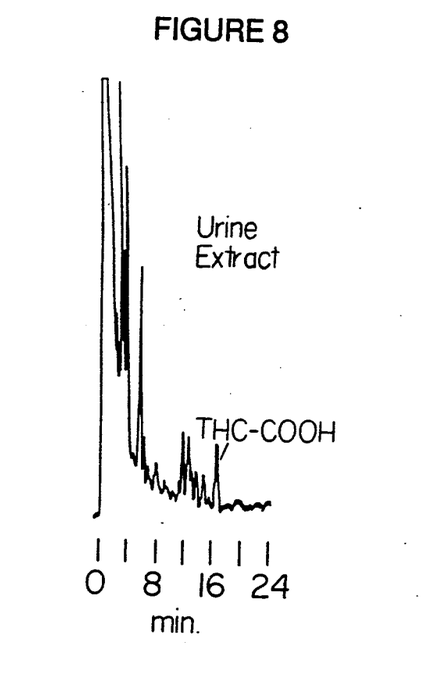
FIG. 8 depicts a typical HPLC chromatogram for an extracted urine sample. The initial concentration of THC-COOH in the urine sample was 250 ng/ml.
Figure 9:
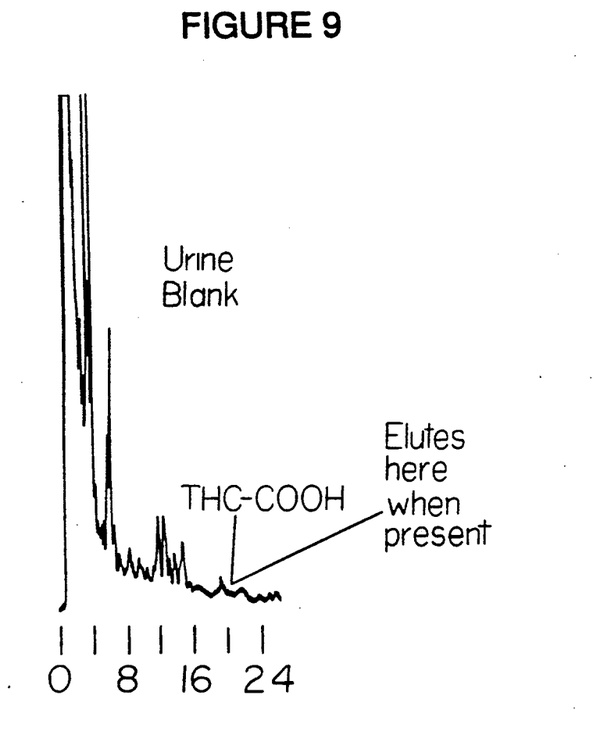
FIG. 9 depicts a typical HPLC chromatogram obtained from an extracted urine blank.

FIGS. 7 through 9 show the detection of non-derivatized THC-COOH using a 25 cm×4.6 mm I.D. (5 micrometer packing) octyldecylsilane HPLC column with ultraviolet detection. The analytical conditions used with this column were a mobile phase consisting of acetonitrile and 2% acetic acid in deionized water (55:45), a flow rate of 2.5 ml/min, column temperature of 30° C., an injection volume of 100 μl, a detector wavelength of 280 nm and a detector sensitivity of 0.004 AUFS. FIGS. 7 through 9 show typical chromatograms obtained from a THC-COOH standard, an extracted urine sample originally containing 250 ng/ml and an extracted urine blank. Table 5 shows typical recoveries of THC-COOH obtained from urine samples extracted using this invention as determined by HPLC with ultraviolet detection. The bonded phase used in these extractions is described in Example 1.

TABLE 5

Absolute recovery of THC-COOH from urine using the bonded phase of Example 1 as determined by high performance liquid chromatography with ultraviolet detection.

| | Absolute Recovery | | |
|---|---|---|---|
| Trial | 25 ng/ml | 50 ng/ml | 250 ng/ml |
| 1 | 98.2 | 109 | 86.3 |
| 2 | 110 | 100 | 88.7 |
| 3 | 86.0 | 110 | 84.8 |
| 4 | 93.6 | 98.3 | 89.9 |
| 5 | 89.2 | 110 | 82.7 |
| Avg. ± S.D. | 95.4 ± 9.4 | 105 ± 5.8 | 86.5 ± 2.9 |

Figure 10:
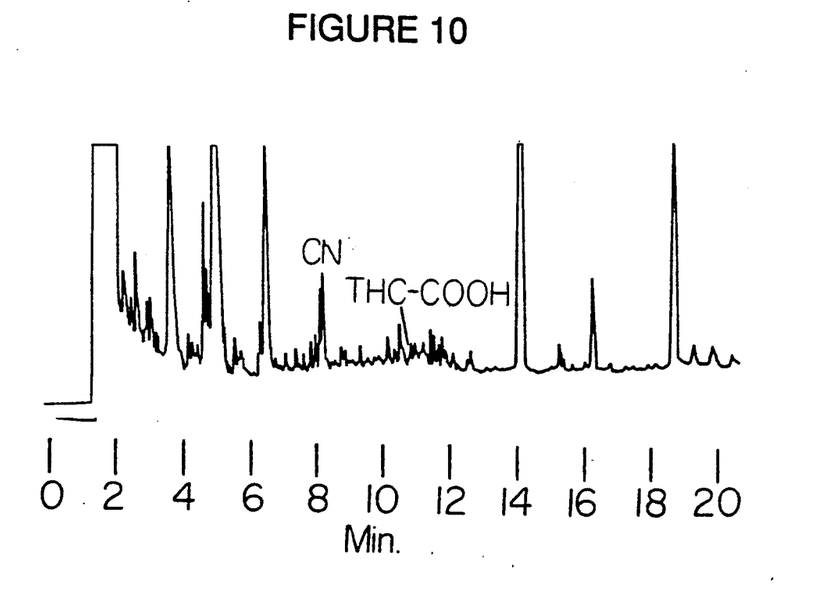
FIG. 10 depicts a typical FID chromatogram obtained from a urine sample extracted using a product manufactured by Analytichem International.
Figure 11:
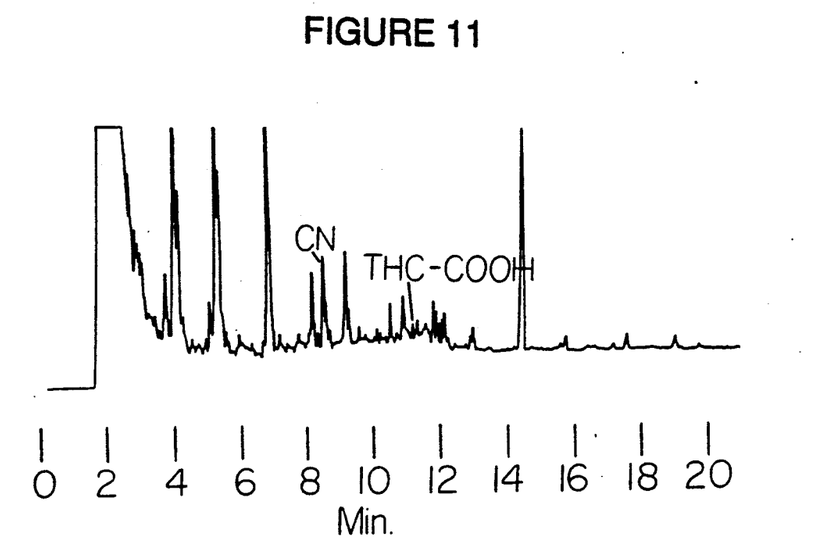
FIG. 11 depicts a typical FID chromatogram obtained from a urine sample extracted using a product manufactured by J. T. Baker.
Figure 12:
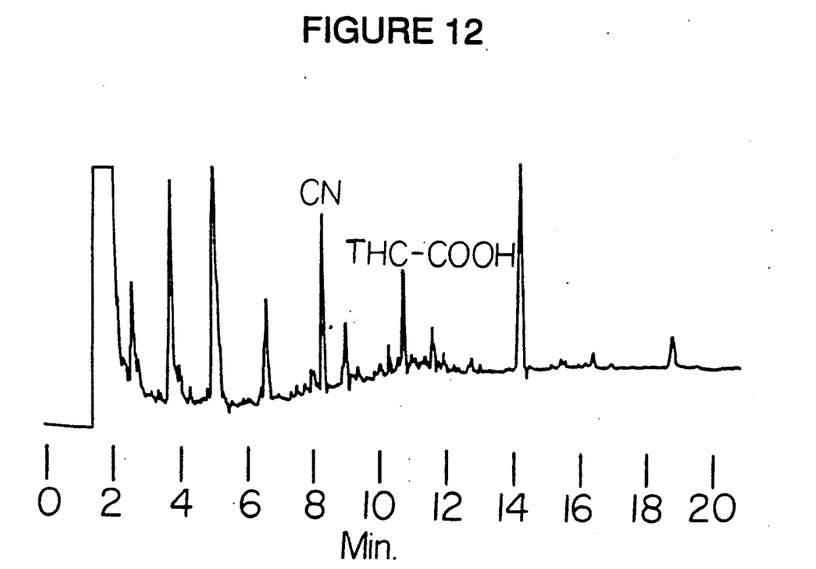
FIG. 12 depicts a urine sample extracted using the invention described in this document. The initial concentration of THC-COOH in the urine samples used in each of these extractions was 50 ng/ml.

The bonded phases and cleanup procedure of this invention provides a much faster, simpler and more efficient isolation and concentration of THC-COOH in urine samples than is possible with currently available phases. FIGS. 10 through 12 show typical GC-FID chromatograms of trimethylsilated THC-COOH obtained from the Analytichem International THC solid phase extraction tube FIG. 10, J. T. Baker Narc-1 solid phase extraction tube (FIG. 11) and this invention (FIG. 12). The original concentration of THC-COOH in the urine samples used for each extraction was 50 ng/ml. The samples extracted using the J. T. Baker Narc-1 solid phase extraction tube were extracted following the instructions enclosed with the tubes at the time of purchase. The samples extracted using the Analytichem International THC solid phase extraction tube were extracted using a procedure published in the Journal of Analytical Toxicology. No instructions were included with the tubes at the time of purchase. Customers were instead referred to the paper by ElSohly et. al..

Recovery of derivatized THC-COOH as determined by GC-MS from each procedure is summarized in Table 6. The bonded phase invention used in the comparison is described in Example 1.

TABLE 6

Comparison of recoveries of THC-COOH from urine using currently available extraction products and the bonded phase of Example 1 as determined by gas chromatography-mass spectrometry.

| Trial | Analytichem | J. T. Baker | Invention |
|---|---|---|---|
| | Absolute Recovery | | |
| 1 | — | 11.7 | 86.4 |
| 2 | — | 2.6 | 83.2 |
| 3 | 33.2 | 2.3 | 80.8 |
| 4 | 4.6 | 0.9 | 83.3 |
| 5 | 34.7 | 7.1 | 94.8 |
| Avg. ± S.D. | 24.2 ± 17.0 | 4.9 ± 4.4 | 85.7 ± 5.5 |
| | Relative Recovery | | |
| 1 | — | 78.3 | 103 |
| 2 | — | 67.3 | 94.1 |
| 3 | 74.0 | 50.0 | 99.5 |
| 4 | 52.6 | 72.3 | 95.8 |
| 5 | 105 | 85.0 | 95.9 |
| Avg. ± S.D. | 77.2 ± 26.3 | 70.6 ± 13.3 | 97.7 ± 3.6 |

Recovery of THC-COOH using this invention is greater than twice the recovery obtained from currently available methods indicating that this invention provides a much more efficient extraction of THC-COOH from urine. As a result of this increased efficiency, use of this invention allows for lower detection limits of THC-COOH in urine and more reliable quantitation of THC-COOH in urine.

What is claimed is:

1. A solid-phase extraction tube packed with a bonded phase product comprising the product generated from the reaction of a silica support and sulfoxyazidosilanes of the formula:

in which R ia an aliphatic carbon chain from two to ten carbon units in length and $R_1$, $R_2$ and $R_3$ are independently selected from the group consisting of halogen, hydroxyl and $C_1$-$C_4$ alkoxy, the product being useful for the solid phase extraction of THC-COOH.

2. The extraction tube of claim 1 wherein the silica support is particulate silica having an average particle diameter of 3 to 177 micrometers.

3. The extraction tube of claim 2 wherein the particulate silica has an average pore size from 60 to 300 angstrom units.

4. The extraction tube of claim 1 wherein the sulfoxyazidosilanes have the formula:

in which $R_4$ is a carbon chain from zero to four carbon units in length, $R_1$, $R_2$ and $R_3$ are independently selected from the group consisting of halogen, hydroxyl and $C_1$-$C_4$ alkoxy, and the product is useful for the solid phase extraction of THC-COOH.

5. The extraction tube of claim 4 wherein the silica support is particulate silica having an average particle diameter of 3 to 177 micrometers.

6. The extraction tube of claim 4 wherein the particulate silica has an average pore size from 60 to 300 angstrom units.

7. A solid phase extraction tube packed with the bonded phase product comprising the product generated from the reaction of a silica support and sulfoxyazidosilanes of the formula:

wherein R is an aliphatic carbon chain from two to ten carbon units in length and $R_1$ and $R_2$ are independently selected from the group consisting of halogen, hydroxyl and ethoxy, the product being useful for the solid phase extraction of THC-COOH.

8. A solid phase extraction tube packed with a bonded phase comprising the product generated from the reaction of silica and sulfoxyazidosilanes of the formula:

wherein $R_1$ and $R_2$ are independently selected from the group consisting of halogen hydroxyl and ethoxy, the product being useful for the solid phase extraction of THC-COOH.

* * * * *